(12) United States Patent
Roques et al.

(10) Patent No.: US 8,414,832 B1
(45) Date of Patent: Apr. 9, 2013

(54) FAST MICRO GAS CHROMATOGRAPH SYSTEM

(76) Inventors: Ned Roques, Lewisburg, WV (US); John Crandall, Lewisburg, WV (US)

( * ) Notice: Subject to any disclaimer, the term of this patent is extended or adjusted under 35 U.S.C. 154(b) by 689 days.

(21) Appl. No.: 12/555,783

(22) Filed: Sep. 8, 2009

Related U.S. Application Data

(60) Provisional application No. 61/095,075, filed on Sep. 8, 2008.

(51) Int. Cl.
*G01N 30/02* (2006.01)
*G01N 30/54* (2006.01)

(52) U.S. Cl. ............ 422/89; 73/23.39; 73/23.4; 96/102; 96/106

(58) Field of Classification Search ............ 422/70, 422/89; 73/23.39, 23.4, 61.53, 61.57, 61.58; 95/87; 96/102, 106; 210/198.2
See application file for complete search history.

(56) References Cited

U.S. PATENT DOCUMENTS

| | | | |
|---|---|---|---|
| 4,096,908 A * | 6/1978 | Lamy | .............................. 165/64 |
| 4,872,334 A | 10/1989 | Watanabe | |
| 5,028,243 A | 7/1991 | Rubey | |
| 5,048,322 A | 9/1991 | Hiller et al. | |
| 5,092,156 A | 3/1992 | Miskolezy | |
| 5,099,743 A | 3/1992 | Rounbehler et al. | |
| 5,108,705 A | 4/1992 | Rounbehler et al. | |
| 5,114,439 A * | 5/1992 | Yost et al. | .......................... 95/18 |
| 5,300,758 A | 4/1994 | Rounbehler et al. | |
| 5,310,681 A | 5/1994 | Rounbehler et al. | |
| 5,551,278 A | 9/1996 | Rounbehler et al. | |
| 5,611,846 A | 3/1997 | Overton | |
| 5,808,178 A | 9/1998 | Rounbehler et al. | |
| 6,209,386 B1 | 4/2001 | Mustacich | |
| 6,217,829 B1 | 4/2001 | Mustacich et al. | |
| 6,311,544 B1 | 11/2001 | Bertrand | |
| 6,427,522 B1 | 8/2002 | Thomas et al. | |
| 6,530,260 B1 | 3/2003 | Mustacich et al. | |
| 6,579,345 B2 | 6/2003 | Munari et al. | |
| 6,607,580 B1 | 8/2003 | Hastings et al. | |
| 6,649,129 B1 | 11/2003 | Neal | |
| 6,952,945 B2 | 10/2005 | O'Brien | |
| 7,303,610 B2 | 12/2007 | Zilloli et al. | |
| 2001/0009647 A1 | 7/2001 | Mustacich | |
| 2005/0247104 A1 | 11/2005 | Hasselbrink et al. | |
| 2005/0268693 A1 | 12/2005 | Hasselbrink et al. | |
| 2005/0287033 A1 | 12/2005 | Thurbide | |
| 2006/0283324 A1 | 12/2006 | Roques | |

FOREIGN PATENT DOCUMENTS

| | | |
|---|---|---|
| WO | WO 92/10748 | 6/1992 |
| WO | WO 2008-030131 A1 | 3/2008 |

\* cited by examiner

*Primary Examiner* — Jan Ludlow
(74) *Attorney, Agent, or Firm* — Sheldon H Parker, Esq.

(57) ABSTRACT

The invention is a chromatography apparatus which comprises at least one capillary column, which has a coil assembly of column material and a small diameter wire coated with an electrically insulating high temperature material encased within a high temperature sheath. The small diameter wire is at least one electrically conductive element co-linear with the column material. Also provided is means for directly resistively heating the at least one capillary column, and means for controlling the temperature of the capillary column. Additionally, the apparatus includes an oxygen gas containing inlet, a hydrogen inlet, an analyte port and a flame region, oxygen delivery means for delivering oxygen through the oxygen inlet to the flame region, a hydrogen and analyte delivery system for delivering hydrogen and analyte to the flame region, and a detector arranged to detect flame emission.

21 Claims, 8 Drawing Sheets

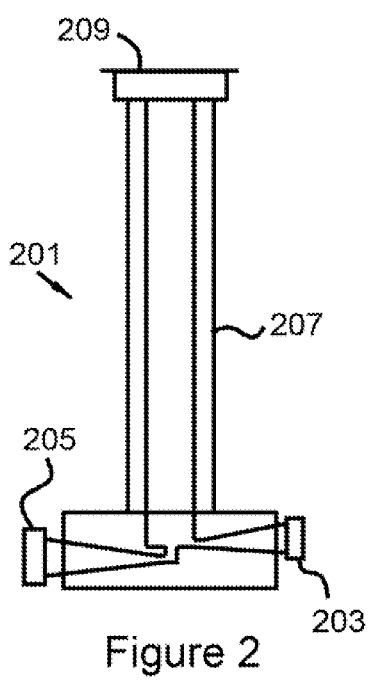
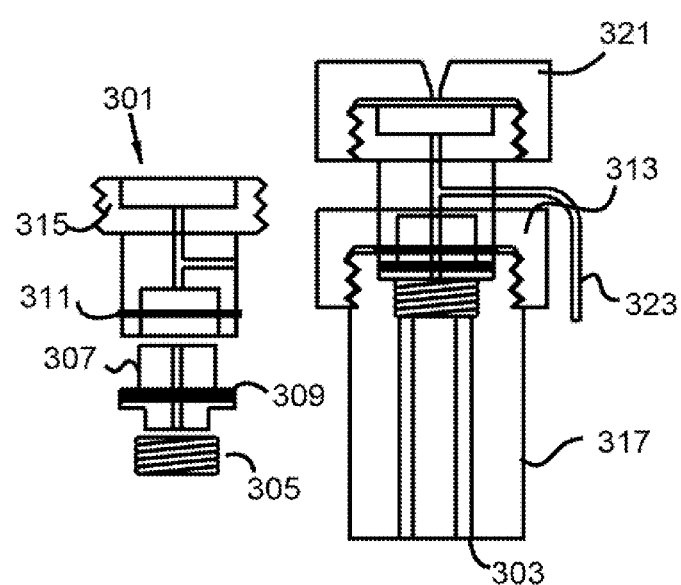
Figure 2
Figure 3
Figure 4
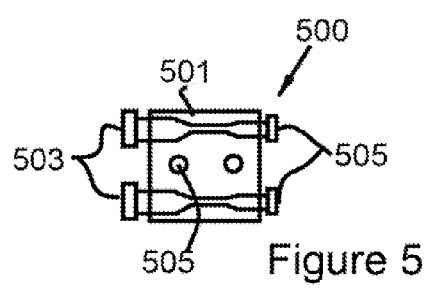
Figure 5

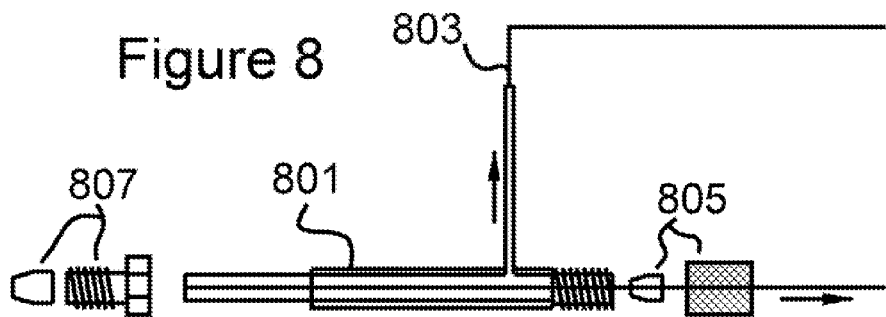
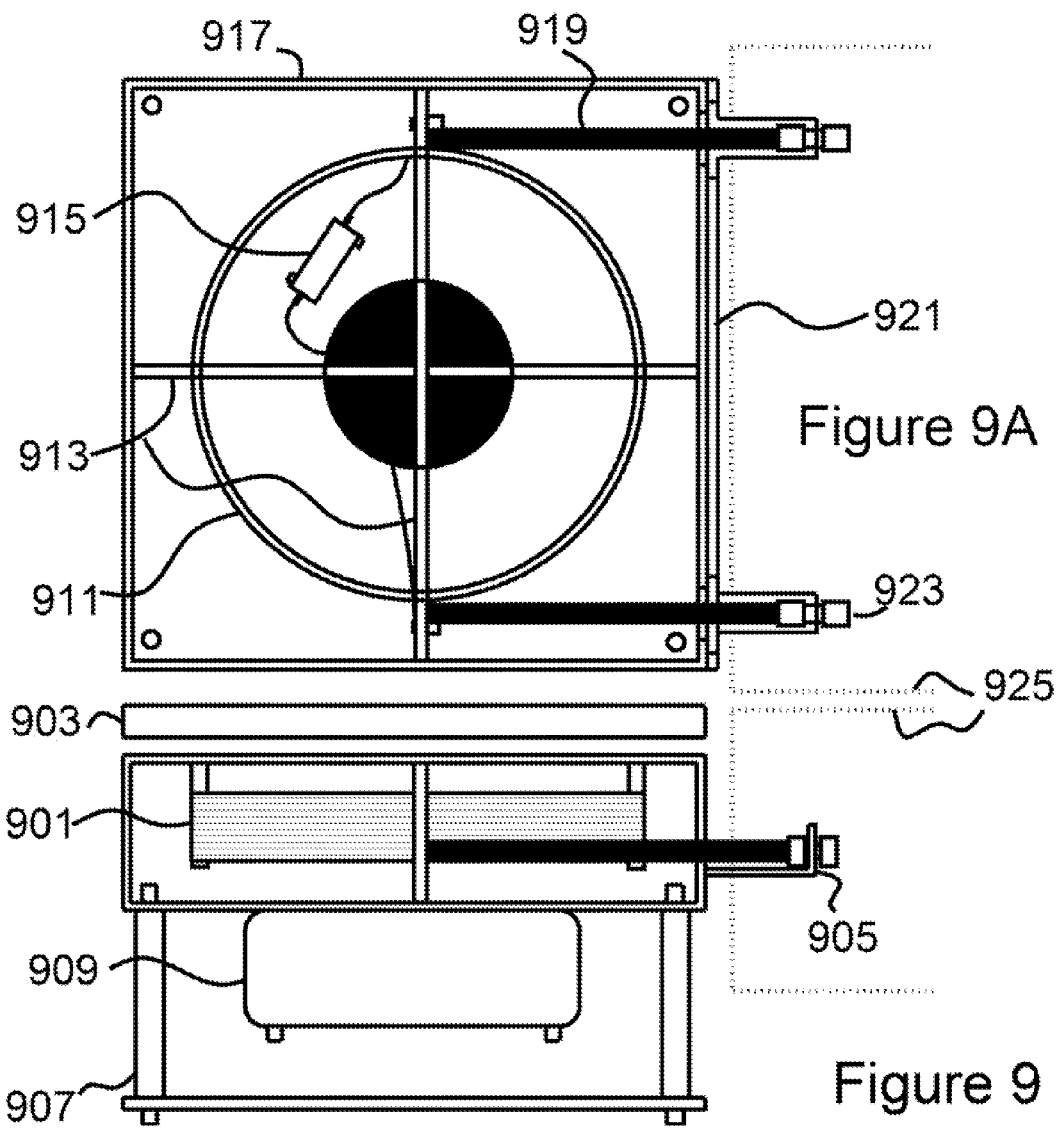

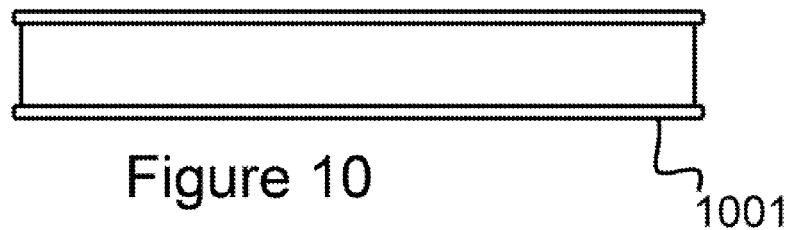
Figure 10
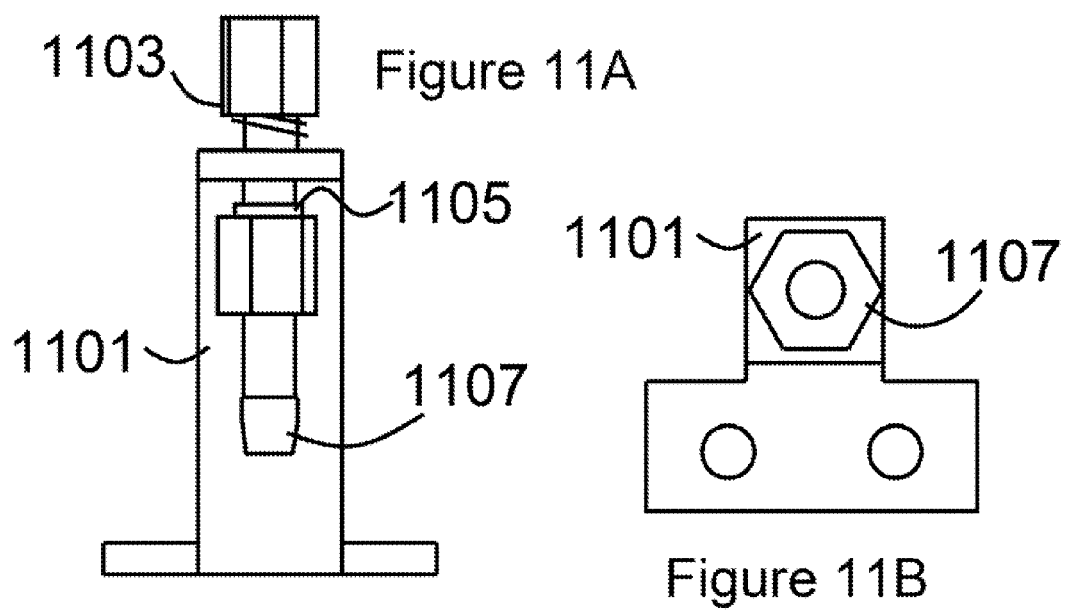
Figure 11A
Figure 11B
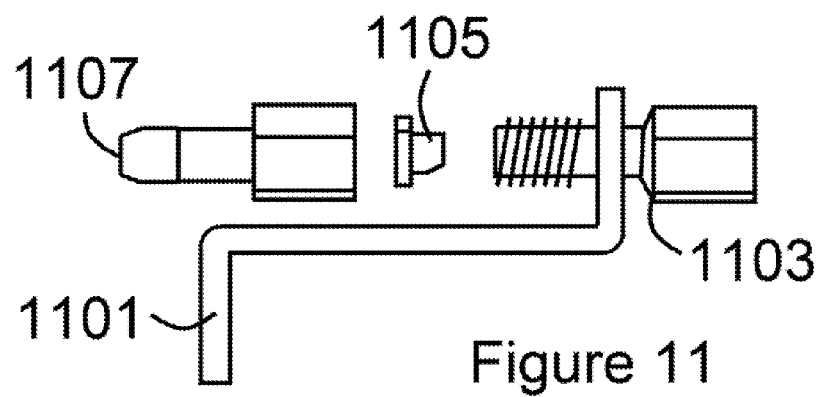
Figure 11

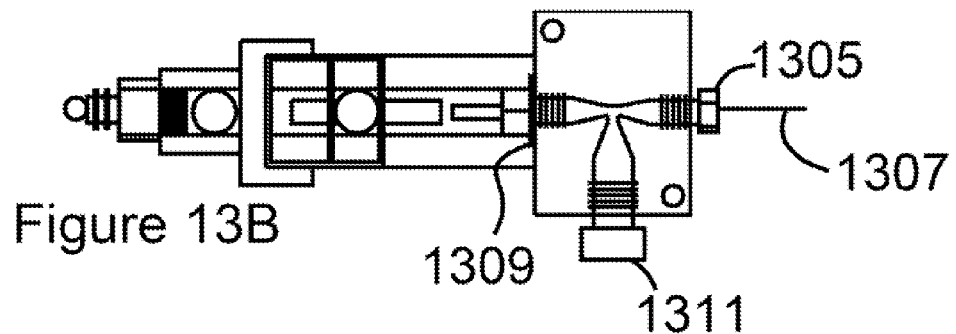
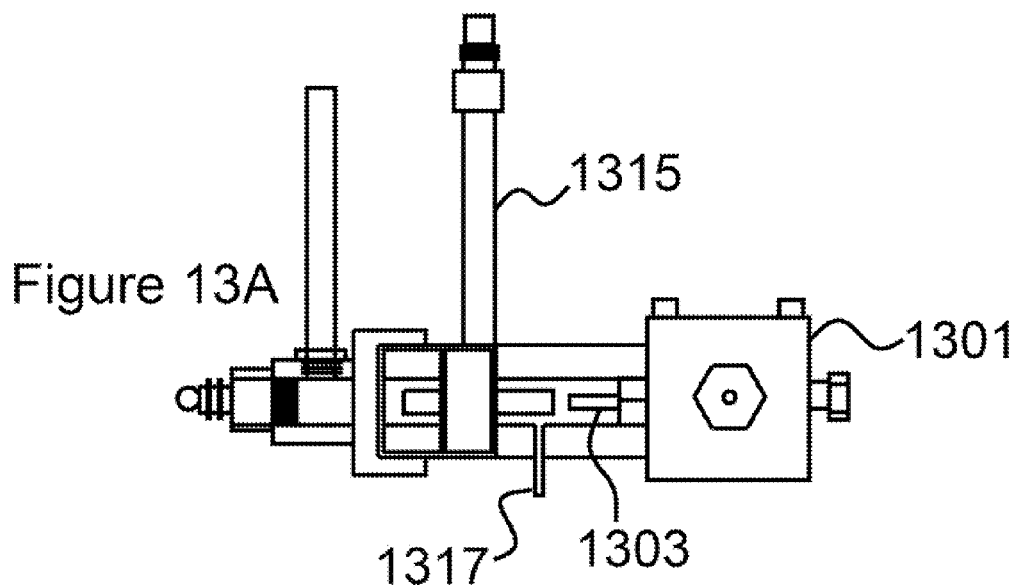
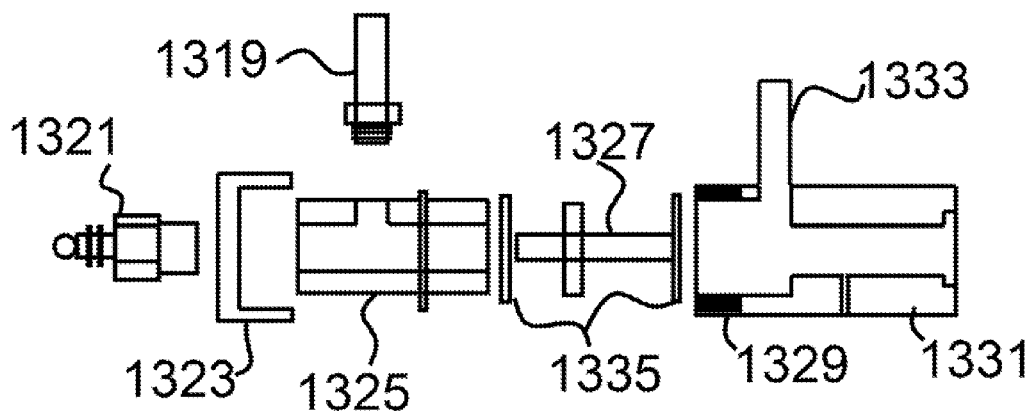
Figure 13

FAST MICRO GAS CHROMATOGRAPH SYSTEM

FIELD OF THE INVENTION

The invention relates to a chromatograph system having a column module and a detector module.

DESCRIPTION OF THE INVENTION

Summary of the Invention

The Sample Processing Module (SPM), as currently designed and tested, consists of three distinct physical arrangements which provide for three distinct modes of operation. Each mode of operation is designed for a specific type of sample introduction (i.e. liquid or gas sample or both) at the GC inlet for differing concentration ranges of solute being analyzed. The individual modes of operation each require their own specific timing sequences which will be described below along with critical physical components and connections.

In accordance with an embodiment of the invention, a chromatography apparatus is provided which comprises at least one capillary column, which has a coil assembly of column material and a small diameter wire coated with an electrically insulating high temperature material encased within a high temperature sheath. The small diameter wire is at least one electrically conductive element co-linear with the column material. Also provided is means for directly resistively heating the at least one capillary column, and means for controlling the temperature of the capillary column. Preferably, the high temperature sheath is fiberglass, or other material providing the same advantageous properties. Preferably, the electrically insulating high temperature material is a high temperature polymer and most preferably it is a polyimide. Preferably, the column material has a size in the range from about 100 µm I.D. to 180 µm I.D.

In accordance with another embodiment of the invention, the chromatography apparatus further comprises a ring member. The capillary column is coiled on the ring member. The ring member is a support member of a relatively low mass material, such as aluminum and the column material and the sensor wire assembly is bundled tightly and compactly wrapped around the ring member.

In accordance with another embodiment of the invention the ring has raised lips proximate its top and bottom edges and such that the column assembly coils are retained on the ring within the raised lips.

In accordance with another embodiment of the invention, the small diameter wire is a sensor wire and a temperature modulation circuit is electrically connected to the sensor wire.

In accordance with another embodiment of the invention, the ring has a wall thickness of under 0.1 inch. Preferably, the wall thickness is under about 0.05 inch, and more preferably, the wall thickness is under about 0.025 inch.

In accordance with still another embodiment of the invention, the small diameter wire has a diameter of less than about 0.01 inch. Preferably, the small diameter wire has a diameter of less than about 0.005 inch, and even more preferably, the small diameter wire has a diameter of about 0.002 inch, that is, between about 0.003 and 0.001 inch. The small diameter wire is fitted with low resistance lead wires and the sensor wire is in intimate, electrically insulated contact with the capillary material, whereby the intimate contact between the sensor wire and the column material and the low mass of each, provides a very small thermal transport delay between the sensor wire and the capillary material, and provides a very fast, accurate temperature feedback control loop.

In accordance with another embodiment of the invention, the capillary column material is an electrically resistive material and a power supply is electrically coupled to the capillary column material and operable for temperature modulated resistive heating of the capillary column material.

In accordance with still another embodiment of the invention, an electric-pneumatic end connector is affixed to each end of the capillary column and provides an electrical contact with the sensor wire and a fluid inlet to a first end the capillary column and a fluid outlet to a second end of the capillary column, each of the end connectors projecting into a heated zone while still being attached to the capillary column. Preferably, the end connectors are stainless steel sheet metal and the connectors are supported by an aluminum material support member. The support member provides an electrical bridge between the capillary column and the end connectors. Electrical conductive wires are attached to the end connectors and routed to a circuit board for power input.

In accordance with still another embodiment of the invention a detector module is provided within the heated zone. Preferably, the detector module is either a flame ionization detector, a flame photometric detector, or a thermal conductivity detector, or combinations thereof.

In accordance with still another embodiment of the invention the overall length of the capillary column and sensor wire combination is preferably on the order of at least two meters. Preferably cooling means is positioned relative to the column module which includes the ring, the sensor wire, and the capillary column, and can be a blower fan positioned to cool at least one component within the column module.

In accordance with still another embodiment of the invention a heater is in heat transfer relationship with a micro-flame detector and is the heat source to the heated zone. The method of operation includes operating the cooling means during the idle and cool down phases of an analytical cycle and turning off the cooling means during temperature programming. Heating control means is provided to control the maximum heating rate that is desired for a given length of column material, wherein the maximum heating rate is a predetermined value based on the high resistance of the metal capillary column material and Ohm's law, and wherein power dissipation is inversely related to length of column material.

The algorithm employed herein prevents what is called integral windup. This is where the algorithm gets a head of steam going and plows through the setpoint while allowing fast heating when the temperature error is large. The algorithm also facilitates tuning of the three PID parameters to achieve "control."

Temperature error is defined as $E_t$. $E_t$ equals the difference between the Target temperature $T_t$ and the actual temperature $T_t$.

$$E_t = T_t - T_a$$

The magnitude of error is defined as $E_m$. $E_m$ equals the absolute value of the temperature error $E_t$ divided by the target temperature $T_t$.

$$E_m = |E_t/T_t|$$

The integral factor is defined as $F_i$. $F_i$ equals one minus the magnitude of error $E_m$.

$$F_i = 1 - E_m$$

The algorithm is only called by the software when the magnitude of error is less than one.

If $E_m<1$, then use the integral $I_f$ the PID control loop as follows:

$$I_f = \Sigma F_i^2 * E_t$$

In accordance with an embodiment of the invention a chromatography apparatus is provided which comprises at least one capillary column, which has a coil assembly of column material and a small diameter wire coated with an electrically insulating high temperature material encased within a high temperature sheath. The small diameter wire is at least one electrically conductive element co-linear with the column material. Also provided is means for directly resistively heating the at least one capillary column, and means for controlling the temperature of the capillary column. Additionally, the apparatus includes an oxygen gas containing inlet, a hydrogen inlet, an analyte port and a flame region, oxygen delivery means for delivering oxygen through the oxygen inlet to the flame region, a hydrogen and analyte delivery system for delivering hydrogen and analyte to the flame region, and a detector arranged to detect flame emission.

BRIEF DESCRIPTION OF THE DRAWINGS

The invention will be described in conjunction with the accompanying drawings, in which:

FIG. 2 shows the injector stem

FIG. 3 shows the septum purge/inlet liner

FIG. 4 shows the trap tube

FIG. 5 shows the trap mounting block

FIG. 8 shows the split system with the Valco splitter

FIG. 9 shows the column module

FIG. 9A shows the column module in plan view

FIG. 10 shows the aluminum mounting ring

FIG. 11 shows the electric/pneumatic end connector in an exploded view

FIG. 11A shows the electric/pneumatic end connector in a top view

FIG. 11B shows the electric/pneumatic end connector in a front view

FIG. 13 shows the critical components that make up the flame ionization detector in a semi-exploded view FIG. 13A shows the critical components that make up the flame ionization detector in side view, and FIG. 13B shows the critical components that make up the flame ionization detector in a top view.

DETAILED DESCRIPTION

It is advantageous to define several terms before describing the invention. It should be appreciated that the following definitions are used throughout this application.

DEFINITIONS

Steric: of or pertaining to the spatial relationships of atoms in a molecule.

Analyte: a substance or chemical constituent that is determined in an analytical procedure, such as a titration. An analyte (in clinical chemistry preferentially referred to as component) itself cannot be measured, but a measurable property of the analyte can.

O.D.: outer diameter

I.D.: inner diameter

FID: Flame Ionization Detector

FPD: Flame Photometric Detector

TCD: Thermal Conductivity Detector

SPM: Sample Processing Module

EPC: Electronic Pressure Control

VSO: Voltage Sensitive Orifice

RSD: Relative Standard Deviation

RTD: Resistance Temperature Device

EPC: Electronic Pressure Control

VOC: Volatile Organic Carbon

Bare: The term bare is used only to differentiate it from a valve and actuator part number combination, as they are usually ordered. Bare is only the valve itself.

Sample Pre-Concentration or Trap Mode

Figure 1:
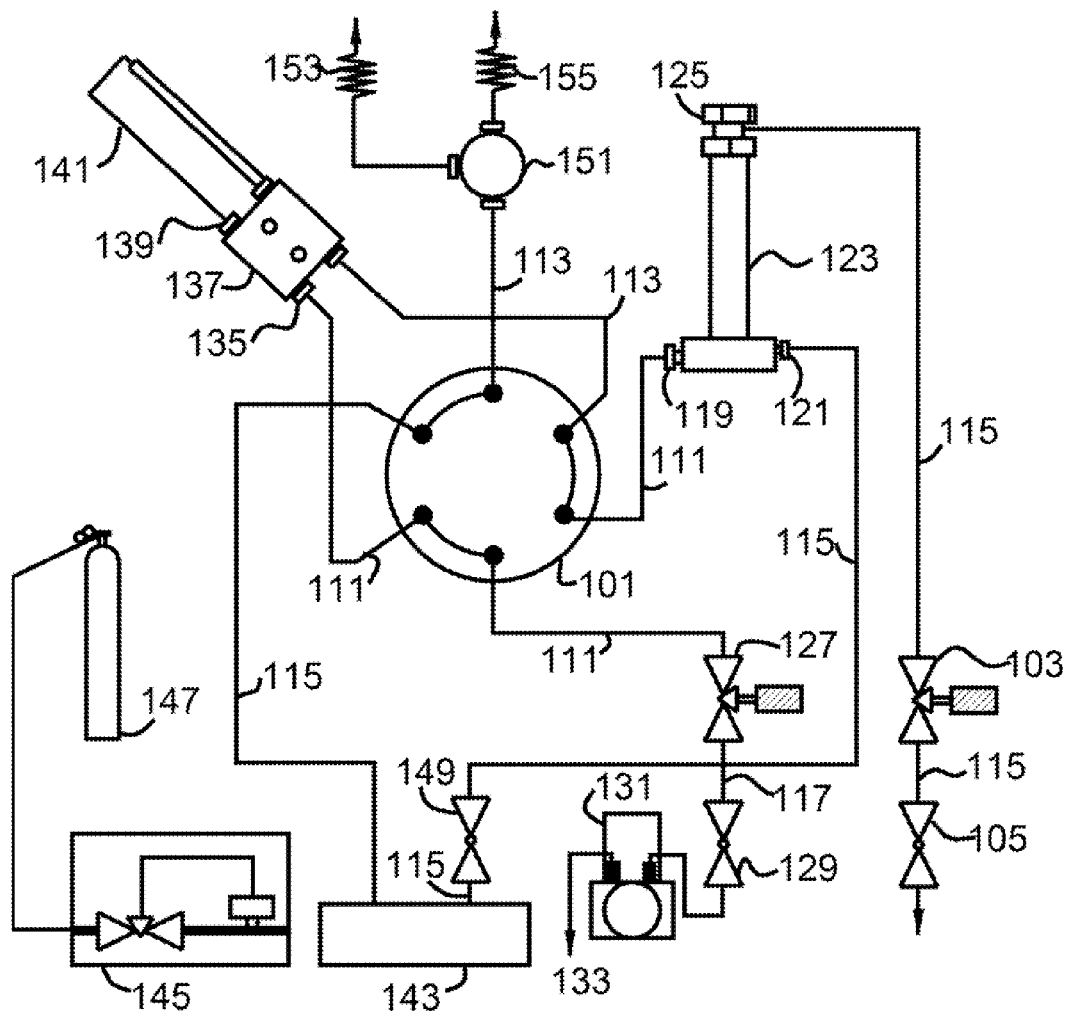
FIG. 1 shows the sample pre-concentration or trap mode

As the name implies, the Trap Mode of operation diverts all samples (gas or liquid) injected into the GC onto an adsorbent trap where concentration of hydrocarbons takes place via polar or steric interactions with the adsorbent material present in the trap tube. The trap tube is then rapidly heated to a known upper temperature at which point the concentrated sample components adsorbed are released into the interstitial spaces of the tube and then back flushed into the separation columns for analysis. The critical components that comprise this mode of operation are shown in FIG. 1.

Component Description $\frac{1}{32}$" 6-port switching valve 101—This valve comprises the heart of the SPM because of its ability to actively direct the flow of carrier gas and sample streams inside the heated zone while minimally affecting the constitution of the sample passing through. The valve chosen is a purchased part from Valco and has the bare part number of D-N-6-WE. Similar chromatography valves are available from other suppliers:

This part number describes a 6-port, two position valve with $\frac{1}{32}$" ports and a Valcon E type rotor material. $\frac{1}{32}$" ports on the valve were chosen in order for $\frac{1}{32}$" O.D. tubing to be used with stainless steel ferrules to enable a reliable seal to be made preventing leaks as a result of thermal cycling of the heated zone. Over the course of the experiments performed using this valve, no leaks developed and all connections remained tight.

The Valcon E rotor material has an upper temperature rating of 225 deg. C. and showed little problem with sample adhesion and peak tailing due to excessive unswept volume. Injection pulses observed from the trap through the valve were very sharp and repeatable. For high temperature work above 225 deg. C., up to a valve temperature of 330 deg. C., the rotor must be changed to a different composition.

Valcon T is the highest temperature rotor material that Valco manufactures. A rotor of this material type was installed in the valve and tested repeatedly at 330 deg. C. with no apparent problems. Injection pulses remained very sharp and repeatable with no noticeable sample component interactions with the valve rotor material. Also, the valve rotors were swapped between the E and T materials several times without generating any leaks internal to the valve.

The only downside as described in the Valco literature has to do with the high temperature Valcon T material sticking to the Internal surface of the valve and freezing up the rotation after cooling from a temperature above 300 dag. C. Valco recommends not using this rotor material below 250 deg. C. for this reason. The experiments performed in the lab at high temperatures showed no signs of this sticking problem.

One possible simple solution for this is to have a software routine created that sets up a cool-down sequence for the heated zone whereby the valve is automatically switched back and forth each time the temperature of the oven drops by, for example, 25 deg. C. thereby limiting the amount of time the rotor material sits static against the polished valve body. This switching would continue until the oven reaches approximately 100 deg. C. and can be safely powered down.

This procedure was done manually in the lab after high temperature testing and as stated earlier no problems were encountered. Actuation of the valve was performed using Valco's Microelectric Actuator (PIN EH) with Right Angle Drive (PIN RAD) and a 3" standoff. The entire valve, standoff, right angle drive and actuator can be ordered as a single unit with a unique part number. Valco's technical support can easily build this part number if contacted.

I.D. with Siltek Coating 111
I.D. with Siltek Coating 113
I.D. 115
I.D. 117
1/16" Fitting Detail 119
1/32" Fitting Detail 121
Inlet Stem 123
Septum Purge Fitting 125
Needle Valve 2 127
Valve 2 N.C. 129
Diaphragm Air Pump 131
To Vent 133
1/32" Fitting Detail 135
Trap Mounting Block 137
1/16" Fitting Detail 139
Trap Tube 141
Pneumatic Manifold/Ballast 143
Electronic Pressure Control 145
Carrier Gas Supply 147
Valve 3 N.O. 149
Valco Low-Volume Tee 151
Flow Resistor 1 153
Flow Resistor 2 155

Injector Stem 201—The Injector stem to be used in the final design is very similar to the design used in testing with the exception of the number and size of ports at the base as shown in FIG. 2.

Only two ports are present: a 1/32" port 203 for carrier gas to enter the stem and a 1/16" port 205 for sample and carrier gas to exit to the 6-port switching valve. The 1/16" port size was chosen so that a 1/16" particulate screen can be inserted between the stem and the tube exiting the stem. This is a last line of defense for preventing particles and other contamination from injected samples from entering the valve body in order to prevent damage to the valve during switching.

The inlet stem is wrapped with a heater tube 207 to provide heat to the upper portion of the stem. Some form of thermal isolation needs to be employed between the stem and the SPM aluminum mounting plate such as short stainless steel standoffs. This will allow the stem to be heated to temperatures above 330 deg. C. without the lower base portion of the stem losing heat to the mounting plate at an excessive rate and consequently being cooler than the top portion.

Septum Purge Fitting Recess 209

Septum Purge/Inlet Liner—The septum purge fitting 301 along with the inlet liner 303, as shown below in FIG. 3, allows for gas near the top of the inlet and more specifically the gas directly beneath the septum to be swept out to vent without contaminating the injected sample stream or internal purge flow.

The septum purge fitting 301 consists of seven key parts each with a specific function. The compression spring 305 provides force to keep the inlet liner firmly seated against the interior floor of the stem. It also provides a free flowing gap for carrier gas to pass from the outside of the glass liner through the spring gaps, over the top of the liner and finally down through the center.

The sealing flange 307 insert provides a nipple for the spring to attach as well as for the sealing o-ring 309 to mount on the opposite side. The nipples on both sides of the wider flange diameter also eliminate extra volume inside the inlet stem 317 and septum purge fitting.

The septum vent fitting contains an external clip ring 311 which holds the inlet sealing nut 313 captive to the septum vent fitting 315. The fitting slides over the top of the dorsal nipple of the sealing flange insert making contact with the sealing o-ring. Tightening the inlet sealing nut onto the inlet stem threads causes the septum vent fitting to compress the sealing o-ring against the sealing flange insert as well as the inner walls of the inlet stem sealing recess. This process seals the entire septum purge fitting to the inlet stem gas tight.

The septum vent fitting has a 1/32" O.D.×0.010" I.D. stainless steel tube silver soldered into the drilled side port to allow septum purge gas to escape to vent through Needle Valve 1 103 and Valve 1 105 shown in FIG. 1.

The septum nut 321 seals the septum to the septum vent fitting to complete the assembly. One important note for the manufacturing of this assembly is the need for holes that are drilled through the septum nut, septum vent fitting and sealing flange fitting to be on center and straight such that when a needle is inserted through the assembly it does not have a tendency to get snagged on the edges of the drilled hole.

Experimental results using this entire assembly showed a drastic reduction in sample contamination from off-gassing of the septum, especially at elevated temperatures above 250 deg. C. Pneumatically, the assembly showed no impact on instrument sensitivity or injection sharpness.

Purge Exhaust Tube 323

Trap Tube—The trap tube 401 shown below in FIG. 4 performs the operation of sample concentration before being injected into the analytical columns for separation.

Packed Particulate Trap 500

Two kinds of traps were tested with both being successful. The first type is a conventional Tenax TA or Tenax GR packed tube of 80/100 mesh material. The tube size was 1/16" O.D.× 0.030" I.D. Bed length was approximately 2" with a final flow of −12 mL/min at 15 in. Hg. The trap is bent in a U shape, open-ended rectangle, in order for the inlet and outlet ends to connect near the same point in the system. The U shape also allowed for the cartridge heater to slide on and off without obstruction.

Experimental results from using this trap configuration were as good, or better than experienced with other commercially available trap technologies. This includes the efficiency with which the trap concentrates analytes, releases the analytes for subsequent injection into the analytical separation columns and the rate at which the trap material desorbs residual components in preparation for another analysis cycle.

An explanation should be made at this point regarding the way in which the trap cleans out in this system, Most systems that rely on concentrating traps adsorb or "load" in one direction and then desorb or "inject" in the reverse direction immediately followed by an extended desorption phase that continues in the reverse direction to clean the trap bed.

While this instrument does adsorb in one direction and desorbs in the opposite direction, the clean-out phase is performed in the "load" direction at an appropriate elevated temperature. Most instrument designers shy away from this approach due to the fear of contaminating the downstream adsorption bed and tubing, however, the use of a trap to concentrate sample analytes implies that sample analyte concentrations are usually small and are regulated from entering the trap by the temperature of the inlet and the glass wool packed inside the inlet glass liner.

Also, due to the small particle size used to pack the trap bed and the small internal diameter of the trap tube, desorption of analytes during injection is very efficient for this system injecting greater than 99% of the adsorbed material into the columns for analysis. This alternative approach to cleaning the trap bed in the adsorb direction has proven to be very effective with no observable contamination from the trap or downstream plumbing during subsequent "blank" analysis. This was true for both gas and liquid sample injections and even more so for the open-tubular trap design described below due to the even greater adsorb/desorb efficiency inherent to open-tubular trapping/distillation mechanisms.

Open-Tubular Trap

The second type of trap tested was open tubular in geometry and consisted of a 0.028" O.D.×0.020-I.D. SS tube bent into the same U shape, open-ended rectangle, of the appropriate length. Then a piece of 320 μm I.D. open-tubular fused-silica column material was cut to a length of 2" and inserted into one leg of the bent tube material until it bottomed out against the backside bend connecting the short leg of the tube. A very small crimp was placed on the outside of the tube at the spot where the column material terminated inside the tube in order to anchor it in place.

Care had to be taken so as not to distort the O.D. of the metal tube to the point where the trap heater adapter tube would not slide easily over the crimp. The trap heater adapter tube is a 1/16" O.D.×0.030" I.D. aluminum tube 2" long that fills the gap between the 0.028" O.D. trap tube and the 1/16" I.D. heater cartridge. Due to the open-tubular nature of the trap, resistance to flow of both sample and carrier gas is much lower than with a conventional packed trap therefore a needle valve (See FIG. 1) was installed in series downstream with the trap flow path to reduce the sampling and cleanout flow to approximately 15 mL/min.

The column material tested for VOC concentrating (nC4-nC9) was GS-CarbonPlot from Agilent. This material performed better for all aspects of VOC concentrating and especially for adsorbing the lighter n-C4 than the packed Tenax GR 60/100 mesh trap tested. For liquid samples GS-GASPRO also from Agilent proved to have the best performance.

Problems were encountered with all open-tubular materials tested when trying to effectively adsorb components lighter than n-C10 with liquid injections. It was later discovered that lowering the internal purge flow rate through the trap during loading to approximately 5 mL/min significantly increased the adsorption for all analytes below n-C10. This produced results comparable to the packed Tenax TA traps tested in the system with liquid samples previously, however, the open-tubular traps are more sensitive to the volume of purge gas delivered through the trap during sample loading.

Longer purge times resulted in the analytes below n-C10 to sequentially desorb through the trap (also known as component "break-through" resulting in lower injected concentrations for these lighter components. Consequently, liquid sample injection timing has a direct affect on the final concentration of light analytes below n-C10 in the trap before transfer to the columns. In order to achieve repeatable results, the sample had to be injected at precisely the same moment in the sample time from analysis to analysis.

This does not necessarily present a problem since the standard operating procedure of the instrument should include as part of its methodology an injection technique that directs sample into the instrument at exactly the same moment during the sample time for each analysis and more preferably the use of an autosampler device that will perform this very precise function for the user.

Trap Mounting Block—The Trap Mounting Block shown in FIG. 5 was designed to connect the parallel ends of the trap tube to the internal plumbing of the instrument in a way that is simple and easily accessible.

A single block of stainless steel 501 is machined with parallel through ports 503 with 1/16" Valco fitting details on the trap receiving side 505 and 1/32" Valco fitting details on the oven side connected by 0.015" diameter holes 507. One-sixteenth of an inch diameter screens are placed at the bottom of the 1/16" fitting details to prevent particulates from the trap bed or inner tubular surface from entering the 6-port switching valve plumbing.

Polymeric ferrules (P/N FS1.5V) from Valco are used to seal the trap to the mounting block. Because of the elasticity of polymeric ferrules, the sealing nuts can be loosened slightly to release the trap from the block without having to completely remove the nuts. Metal ferrules and 1/32" SS tubing are used on the oven side to provide for rugged, leak free connections.

Needle Valve 1—The purpose of this needle valve is to reduce the septum purge flow down to approximately 5 mL/min at 15 psi of hydrogen pressure. A flow of 5 mL/min was tested in the lab and appeared to be an adequate flow rate to prevent septum contamination from entering the internal purge sample stream while at the same time minimally affecting sample transfer to the trap. Valco P/N CNV1A10S1 is a low-flow needle valve that is slated for use in this position.

Needle Valve 2—This needle valve is used to control the sample flow through the trap during gas sampling as well as liquid sampling. During trap clean-out this needle valve also limits the flow rate through the trap. In the gas sampling mode, the trap clean-out flow will be higher than the sample flow rate due to the different pressures and viscosities of air and hydrogen in the two different parts of the cycle. For liquid samples the internal purge flow that directs sample onto the trap and the clean-out flow will be identical.

In testing, the needle valve was set anywhere between 5 and 25 mL/min depending on the type and the needs of the analysis with excellent results. In general, lower sample flow rates corresponded with better adsorption on the trap for lighter molecules that have low break-through volumes. Valco P/N CNV1A50S1 should be a good fit for this requirement.

Flow Restrictors 1 & 2—Both flow restrictors are installed between the low volume splitter tee and the two columns in order to increase the system operating pressure above what would normally be needed to drive the correct linear velocity of the carrier gas through the short columns that are used. These restrictors are generally 50 um I.D. deactivated fused silica and are necessary for columns greater than 100 um in I.D. The relative restriction values of both restrictors (i.e. their lengths) must be exactly the same if flow rates through the two different columns are to be equal. This is important because different flow rates through two separate columns of the same I.D. will result in unequal sample splitting from the trap onto both columns, which translates to different sensitivities between the two channels.

Electronic Pressure Control—Two kinds of electronic pressure control were tested on the system. The first utilized a Pneutronics VSO valve coupled to an independent 0-100 psi pressure sensor arranged into a feedback control loop.

Repeatability results using this setup were very similar to or better than commercially available products using this type of pressure control.

The second kind of EPC tested consisted of a purchased unit containing VSO valve, pressure sensor, and feedback control circuitry in one package. The unit was purchased from Parker/Pneutronics and required a 0-3V input signal to control over a 0-30 psi output pressure range. The product was pre-calibrated from the factory and produced outstanding results relative to the stand alone VSO valve configuration. Area RSD's for nC4-nC9 were on the order of 1.0-1.5%, which is roughly half the value of similar products on the market Manifold/Ballast—A pressure ballast was used at the output of the EPC system in order to provide a pressure reserve to smooth out transient pressure spikes due to abrupt changes in flow rates in the course of an analytical cycle. A volume of 5 mL bored into a manifold was used as the entry point for pressurized carrier gas from the EPC outlet. All tubes and valves providing pressurized gas to the system emanated from this manifold. The exact minimum volume needed to maintain a very smooth output pressure from the EPC and consequently a very repeatable system is not known at this time. More testing would have to be performed to determine the optimal volume.

Pneumatic Diaphragm Pump—The diaphragm pump provides vacuum for drawing ambient pressure samples through the inlet and trap for concentrating. It is positioned as the last element in the sample flow path in order to prevent contact with the sample components before entering the trap. Flow rates through the trap should rarely, if ever, exceed 200 mL/min, Therefore large pumping volumes are not necessary from the pump.

The more important specification is the vacuum that can be generated and maintained by the pump during sampling. The ability to draw at least a 15 in, Hg vacuum at 200 mL/min. should be sufficient for this system. Another critical requirement of the pump is its ability to provide a free flowing path for a gas stream while not activated. This is important for internal sample purge flows as well as trap clean-out flows since these two operations share the same flow path, KNF and Hargraves are two companies that manufacture products that meet the standards of the present invention.

Tubing—With the exception of Flow Restrictor 1 and 2 all tubes in the heated zone are stainless steel, 1/32" O.D. The inside diameters of the various tubes are different and are differentiated in FIG. 1. The tubes that are 0.020" I.D. are used to minimize the pressure drop in the flow path during gas sampling when air is being drawn through a packed trap.

Restek Siltek Coating—All components inside the instrument heated zone that are exposed to sample components are to be coated with Restek's Siltek coating. This is to prevent the catalytic decomposition of reactive compounds on the inner stainless steel surface of the tubing making up the flow paths. The parts that are to be coated are: Inlet Stem, Low-Volume Splitter Tee. Trap Tube, Trap Mounting Block, and all tubing marked s in FIG. 1 above.

Analysis Sequence Description

The following is a step-by-step description of an analytical cycle as tested in the lab. Refer to FIG. 1 for clarity.

1. Idle State—The EPC is providing constant pressure carrier gas to the ballast manifold. Pressurized carrier gas flows from the ballast manifold through ports 4 and 5 of the switching valve supplying a constant flow of carrier gas to the two column sets. Both valves 2 and 3 are de-activated, which supplies pressure to the inlet stem, but no flow through ports 1-6 and 2-3 of the switching valve and trap tube due to the normally closed operation of valve 2. Valve 1 is also de-activated which allows septum purge gas to flow out to vent at a rate determined by the setting of needle valve 1.

2. Sampling

Gas Mode—Valves 1, 2, and 3 activate simultaneously along with the diaphragm air pump. This shuts off pressure to the Inlet stem and Opens a pathway for sample to flow from the top of the inlet stem through the trap tube and out to vent through the air pump. Due to the sub-ambient pressures generated In the inlet stem by the sample pump, valve 1 shuts to prevent a reverse-flow condition of gas through the septum purge fitting which would contaminate the gas sample stream entering from the top of the inlet stem. During the Sampling period in the gas mode of operation, gas sample is being drawn through and concentrated on the trap tube for subsequent thermal desorption later in the analysis cycle. The sampling flow rate through the trap tube is largely determined by the setting of needle valve 2.

Liquid Mode—In this sampling mode only valve 2 is activated. This allows a stream of carrier gas to flow inside the inlet stem, flushing the inlet glass liner contents into the trap tube for concentrating and finally forcing the remaining gas out to vent via the sample pump (not activated). The septum purge flow continues as in the idle state to prevent septum contamination from entering the sample purge stream. As with the gas sampling mode, the flow rate through the trap tube is controlled by the setting of needle valve 2.

3. Pressure Equilibration/Trap Heating—After the sample time has ended, valve 2 de-activates causing an abrupt change in flow through the system. This also causes the EPC to oscillate, momentarily disrupting the overall system pressure. The system sits in an idle state for what is called the Equilibration Period where the pressure in all components and tubes stabilizes to the EPC setpoint. With the pressure stable, the trap heater activates and ballistically heats to its upper temperature setpoint in preparation for sample backflush into the separation columns.

4. Sample Backflush—When a preset amount of heating time has elapsed, the sample is backflushed (injected) off of the trap tube into the separation columns by the momentary activation of the 6-port Switching valve. Only the 6-port valve switches states, which connects ports 3-4, 5-6, and 1-2 thereby disconnecting ports 2-3, 4-5, and 6-1. This alters the flow paths such that carrier gas pressure from the ballast manifold pushes the heated trap gas backward off of the trap tube, through ports 6-5 and into the low-volume tee for splitting to the individual separation columns.

During this time gas continues to flow through the inlet stem and out of the septum purge fitting but not through the glass-liner since valve 2 remains in its de-activated state. When the backflush of the trap tube is complete the 6-port switching valve rotates back to its original position followed by the immediate activation of valve 2. Simultaneous with the beginning of the sample backflush is the data acquisition from the analyte detectors along with the temperature programming of the separation columns.

5. Trap Clean Out—With the trap tube heater still at its upper temperature setpoint, flow through the trap tube is now exactly as it was during the loading of the trap during liquid sampling (i.e. in the "forward-flush" direction). Any residual components left in the trap tube are flushed out to vent in preparation for the next analysis cycle.

6. Trap Cool-Down—When the trap tube clean out time has elapsed, the trap tube heater deactivates and a cooling fan (not shown) activates to provide forced convective cooling to the trap tube and heater assembly. Valve 2 deactivates stopping the flow through the trap in order for the trap to cool down under static flow conditions thereby preventing the "re-loading" of the trap from any minute residual compounds in the inlet stem.

Depending on the column temperature programming parameters, the separation of compounds and data acquisition could still be ongoing in the separation columns and detector. The system is now back in the idle state awaiting the completion of the column temperature program(s).

7. Column Cool-Down—At the completion of the column temperature program cycle(s), the column cooling fans (not shown) activate and return the column temperature(s) to their original setpoints thereby readying the system for another analytical cycle. The system has two independently heated separation column modules that may or may not be in synchronous operation. This means that the column module with the longer temperature program will dictate the overall length of the analytical cycle.

The SPM including the Valco 6 port switching valve has been configured to perform other types of chromatographic operation. Techniques taking advantage of column material selectivity such as backflush, heartcut and other common chromatographic column switching applications have been tested. These techniques can be used on both gas and liquid samples using split and split-less sampling technique, with and without the trap.

Sample Loop Mode

Figure 6:
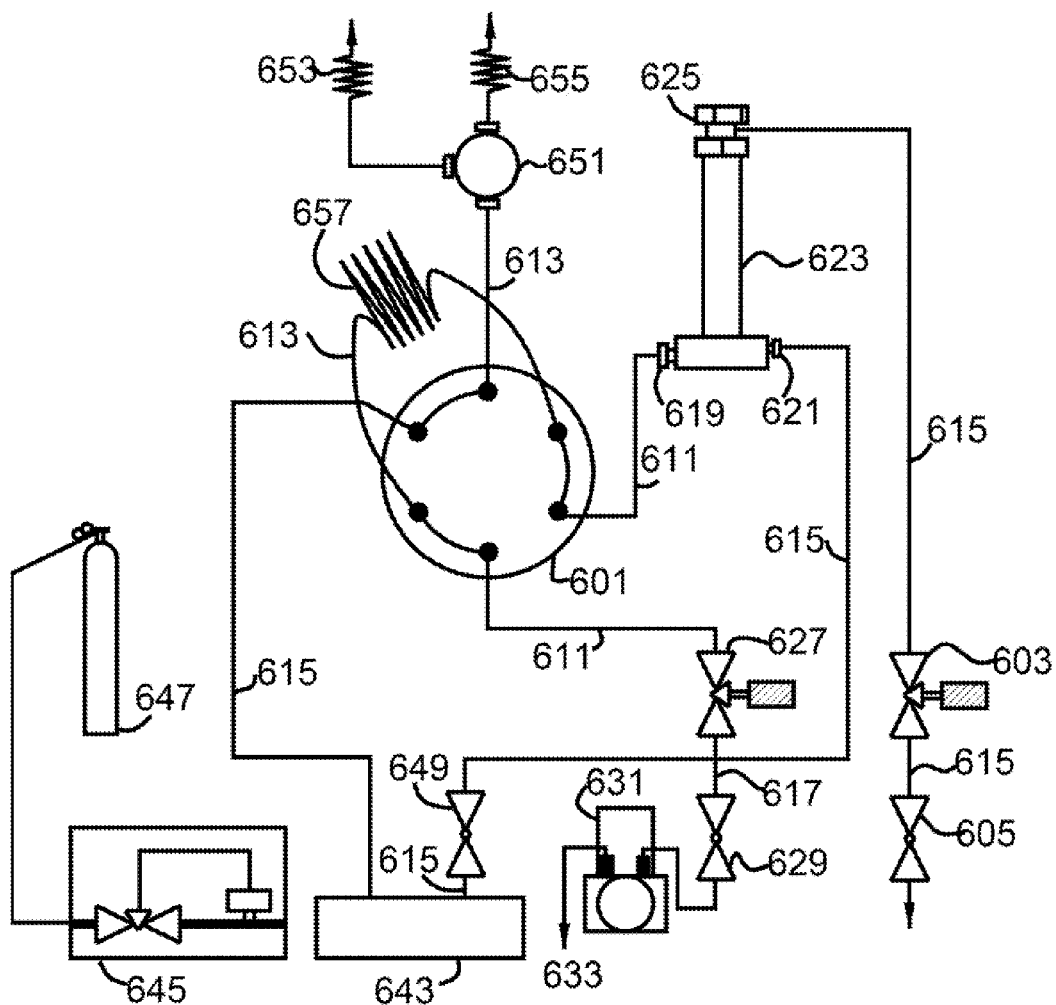
FIG. 6 shows the sample loop mode

The Sample Loop Mode of operation is very similar to the configuration of the Trap Mode with the exception that the trap is replaced by a loop of tubing 601 between ports 3 and 6 of the 6-port switching valve as shown in FIG. 6.

This configuration allows for the analysis of high concentration gas samples (>5 ppmv) since only the volume of the sample loop is injected into the separation columns and no concentration is performed prior to the injection. The internal volume of the sample loop can be adjusted by installing loops of different sizes to accommodate an even wider range of sample concentrations. Analyte discrimination due to uneven adsorption onto the trap packing material is completely eliminated when using the Sample Loop Mode since all gas contained in the sample loop is injected directly.

With the appropriate detector, this allows for the analysis of permanent gases that cannot be concentrated using a trap (e.g. nitrogen, oxygen, carbon dioxide, methane). Also, the mass of sample injected into the separation columns is precisely defined by the internal volume of the sample loop and is extremely repeatable as opposed to the Trap Mode where sample is exposed to the process of adsorption/desorption and then backflushed into the separation columns as a function of time rather than exact volume.

Results achieved in the lab using the Sample Loop Mode of operation showed excellent chromatographic results including repeatability and analyte peak shapes. No signs of peak tailing as a result of excessive unswept volume in the switching valve or tubing connections were evident. Preliminary limits of detection appeared to be around the 1 ppm level for nC4-nC9 hydrocarbons.

The sample loop tube used in testing was 1/32" O.D×0.010" I.D. stainless steel connected to the 6-port switching valve with stainless steel ferrules. The final design will have the inner surface of the tube Siltek coated from Restek to prevent sample decomposition. With the exception of the sample loop, all physical components that make up this module are identical to those found In the Trap Mode of operation. There is, however, a difference in the sequence of events that define the analytical cycle. Those will be described in the section below.

Analysis Sequence Description

The following is a step-by-step description of an analytical cycle as tested in the lab. Refer to FIG. 6 for clarity.

1. Idle State—The EPC provides constant pressure carrier gas to the ballast manifold. Pressurized carrier gas flows from the ballast manifold through ports 4 and 5 of the 6-port switching valve supplying a constant flow of carrier gas to the two column sets. Both valves 2 and 3 are de-activated, which supplies pressure to the inlet stem, but no flow through ports 1-6 and 2-3 of the switching valve and sample loop due to the normally closed operation of valve 2. Valve 1 is also de-activated which allows septum purge gas to flow out to vent at a rate determined by the setting of needle valve 1.

2. Sampling—Valves 1, 2, and 3 activate simultaneously along with the diaphragm air pump. This shuts off pressure to the inlet stem and opens a pathway for sample to flow from the inlet stem through the sample loop and out to vent through the air pump. Due to the sub-ambient pressures generated in the inlet stem by the sample pump, valve 1 shuts to prevent a reverse-flow condition of gas through the septum purge fitting which would contaminate the gas sample stream entering from the top of the inlet stem. During the sampling period in the gas mode of operation, the gas sample is being drawn through the sample loop for subsequent injection later in the analysis cycle. The flow rate through the sample loop is largely determined by the setting of needle valve 2.

3. Sample Injection. Immediately following the Sampling time, when the diaphragm sample pump deactivates, the 6-port switching valve actuates which connects ports 3-4, 5-6, and 1-2 thereby disconnecting ports 2-3, 4-5, and 6-1. This alters the flow paths such that carrier gas pressure from the ballast manifold forces the entire contents of the sample loop through ports 6-5 and into the low-volume tee for splitting to the individual separation columns. Data acquisition from the sample detectors begins at this point along with the beginning of the temperature program for both column modules. The injection takes place for a period of time that is definable in the instrument method in software, but during system testing this value was on the order of 1 second.

4. Sample Loop Clean-Out—When the Sample Injection time elapses, valves 1 and 3 deactivate along with the S-port switching valve. This re-establishes carrier gas pressure to the inlet stem which starts a flow of gas through both the septum purge fitting and the sample loop path thereby flushing any residual components in the sample loop out to vent through the diaphragm air pump. Sample and clean-out flow rates through the sample loop are controlled by needle valve 2. When clean-cut is complete, valve 2 deactivates which returns the system to its idle state. During this time period chromatographic separations are occurring independently in the two column modules.

5. Column Cool-Down—At the completion of the column temperature program cycle(s), the column cooling fans (not shown) activate and return the column temperature(s) to their original setpoints thereby readying the system for another analytical cycle. The system has two independently heated separation column modules that may or may not be in synchronous operation. This means that the column module with the longer temperature program will dictate the overall length of the analytical cycle.

Split Injection Mode

The Split Injection Mode of operation allows for the injection of high concentration liquid samples without the undesirable effects of overloading the separation system. The basic functionality of a split injection inlet is as follows. A liquid sample (1-2 uL) is injected into a heated inlet that is under constant pressure from one carrier gas entry port near the Injection point and has two exit ports near its base. Exit port one is the separation column or a tube that connects with the separation column while exit port two is a much higher flow rate exhaust path whose flow rate is completely user adjustable.

This dual exit port arrangement sets up a condition where the flow of gas (including vaporized sample) from the top of the inlet is split at the base to allow a certain fraction of the total flow to pass through one port while the remaining fraction exits. through the other. By adjusting the split ratio between the column port and the exhaust port, exact quantities of sample can be diverted into the column to match its capacity and resolution. Typical split ratios (exhaust flow: column flow) vary between 25:1 up to 250:1 depending on the column internal diameter and desired volume to be transferred to the column for separation.

0.020" I.D. with Siltek Coating 611
0.010" I.D. with Siltek Coating 613
0.010" I.D. 615
0.020" I.D. 617
1/16" Fitting Detail 619
1/32" Fitting Detail 621
Inlet Stem 623
Septum Purge Fitting 625
Needle Valve 2 627
Valve 2 N.C. 629
Diaphragm Air Pump 131
To Vent 633
Pneumatic Manifold/Ballast 643
Electronic Pressure Control 645
Carrier Gas Supply 647
Valve 3 N.O. 649
Valco Low-Volume Tee 651
Flow Resistor 1 653
Flow Resistor 2 655
Sample Loop 657

Figure 7:
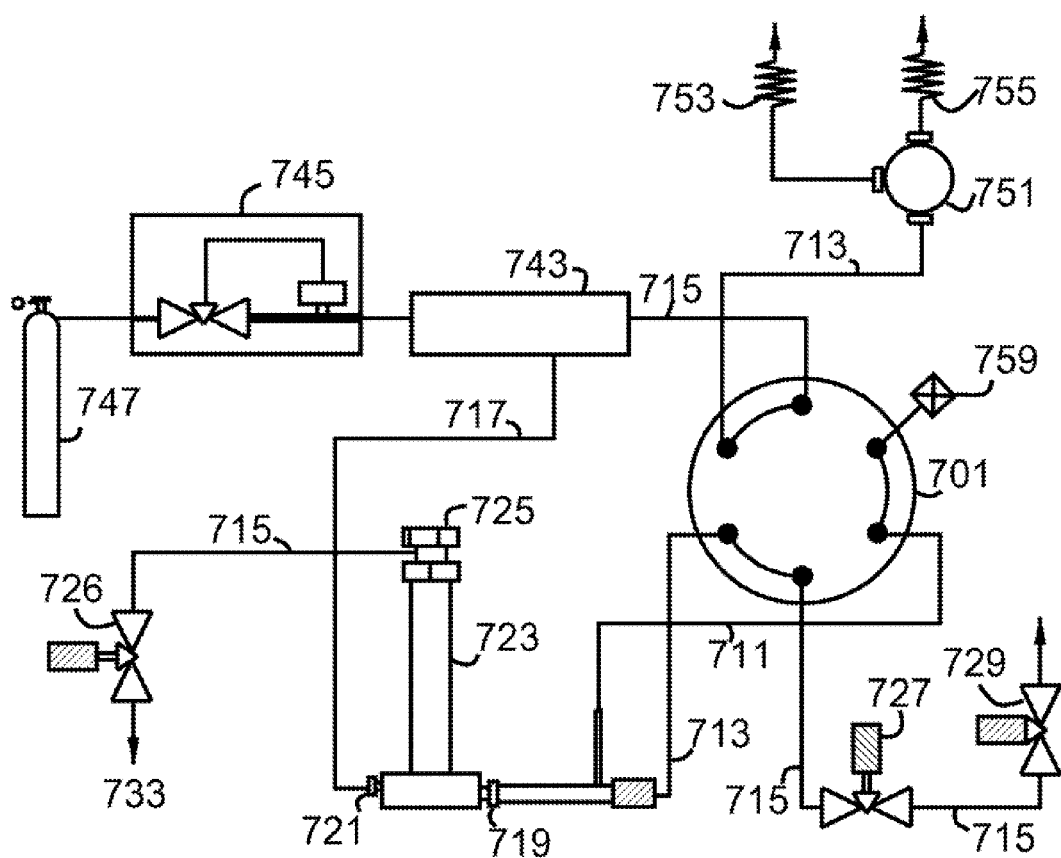
FIG. 7 shows the split injection mode

The design created to implement a Split Injection Mode for the new instrument is shown in FIG. 7.

0.020" I.D. with Siltek Coating 711
0.010" I.D. with Siltek Coating 713
0.010" I.D. 715
0.020" I.D. 717
1/16" Fitting Detail 719
1/32" Fitting Detail 621
Inlet Stem 723
Septum Purge Fitting 725
Needle Valve 1 726
To Vent 733
Needle Valve 2 727
Proportional Valve N.C. 729
Pneumatic Manifold/Ballast 743
Electronic Pressure Control 745
Carrier Gas Supply 747
Valco Low-Volume Tee 751
Flow Resistor 1 753
Flow Resistor 2 755
Plugged Port 759

All of the critical components used to implement the split system shown in FIG. 7 are identical to those found in the previous two modes of operation with the exception of the Valco Splitter 801 which is shown in FIG. 8.

The Valco Splitter allows for the gas stream to be split in a linear fashion across the face of the tube exiting to the separation columns rather than an angled split path that is generally found when using a Tee type fitting, which causes an abrupt change in direction for the sample stream, This "linear" flow arrangement provides for a more repeatable split pattern from analysis to analysis.

All tubing used in the system is 1/32" O.D. stainless steel for making secure connections. The tubing inside diameters are shown in FIG. 7. The 0.020" I.D. tubes are used to reduce the amount of flow restriction in the exhaust split 803 vent flow path due to the larger flow rates that will generally pass through this path.

1/32" Nut & Ferrule 805
1/16" Nut & Ferrule 807

The purpose of using the 6-port switching valve in this arrangement is to provide a clean independent carrier gas source for the separation columns when the system is not in the inject mode. This enables the transfer of sample from the inlet to the separation columns to be terminated at any time after the physical Injection of sample has been made into the inlet stem. An important consequence of this is that the inlet stem can flush itself of undesirable, heavy molecular weight contaminates that tend to have a longer residence time in the inlet without getting loaded into the separation columns. The sequence of events that characterize the Split Injection Mode analysis cycle are listed below. Please refer to FIG. 7 for clarity.

Analysis Sequence Description

1. Idle State—The EPC provides a constant pressure carrier gas source to the separation columns through ports 5-4 of the 6-port switching valve. Constant pressure is also provided to the inlet stem directly through the 1/32" fitting detail located at the bottom of the stem. From this point gas flows up around the outside of the glass liner and out through the Septum Purge Fitting exhaust tube at a rate determined by the setting of Needle Valve 1.

A second stream of gas flows back down the center of the glass liner and into the Sample Split Vent tube. This flow path extends through ports 3-2 on the 6-port switching valve and then through Needle Valve 2 and finally the N.C. (Normally Closed) Proportional Valve and out to vent. The flow rate through this path is largely determined by the setting of the N.C. Proportional Valve in software and is generally set to around 5 mL/min. Flow through the Exhaust Split Vent tube is blocked by the plug in port 6 on the 6-port switching valve.

2. Sample Injection—The Sample Injection period starts when the 6-port switching valve actuates to its alternate position connecting ports 1-2, 3-4, and 5-6 thereby disconnecting ports 2-3, 4-5, and 6-1. Simultaneous with the 6-port valve actuating, the N.C. Proportional Valve opens to its widest position to create the high exhaust vent flow rate which is now controlled by Needle Valve 2.

Carrier gas flow through the inlet stem is now being split to the separation columns through the Sample Split Vent tube and ports 3-4 on the switching valve and at a much higher rate to vent through the Exhaust Split Vent tube and ports 1-2 on the switching valve.

When the Sample Injection period starts, a software adjustable delay must elapse before a signal is given to physically inject sample into the inlet stem. This delay is to allow the EPC to recover from oscillations due to the abrupt change in total system flow that accompanies the opening of the N.C. Proportional Valve. At the end of this delay the data acquisition on the detector system will begin as well as the column temperature programs.

3. Idle Transition—When the Sample Injection time ends (user selectable time), the 6-port switching valve returns to its idle state thereby terminating the flow of sample from the inlet to the separation columns and returning a clean supply of gas for subsequent component separation. It is at this time that the N.C. Proportional Valve begins to slowly close to its original 5 mL/min flow rate setting. The reason for the slow closing of this valve is to prevent an abrupt change in flow rate in the system during the start of the component separations in the columns that are undergoing temperature programming. Preventing this abrupt flow rate change prevents the EPC from oscillating which keeps the column head pressure stable. When the N.C. Proportional Valve reaches its low flow setpoint the system is pneumatically in its idle state awaiting the end of the column temperature programs.

Column Cool-Down—At the completion of the column temperature program cycle(s), the column cooling fans (not shown) activate and return the column temperature(s) to their original setpoints thereby readying the system for another analytical cycle. The system has two independently heated separation column modules that may or may not be in synchronous operation. This means that the column module with the longer temperature program will dictate the overall length of the analytical cycle.

Column Module

The separation column for the invention concept is housed in a self-contained module where each unit consists of all of the electrical controls and hardware necessary for temperature programming and cooling independent of the other modules in the instrument. A functional diagram of a Column module is shown in FIGS. 9 and 9A Each module is capable of rapid temperature programming through the use of resistively heated metal capillary column material. The material used in prototype testing ranged in size from 100 um I.D. to 180 um I.D.

Component Description

Sheathed Column Material 901—In order for rapid temperature programming to be possible,
some form of temperature sensing must be incorporated very near to the metal column material that is being resistively heated. This is accomplished by inserting both the column material and a very small diameter wire (0.002" dia.) coated with electrically insulating, high temperature polyimide resin co-linearly into a high-temperature fiberglass sheath. The small diameter wire is then fitted with low resistance lead wires and used as a RTD device for the feedback control loop that provides the temperature modulation. Due to the intimate contact between the sensor wire and the column material and the low mass of each, the thermal transport delay between the two is very small which results in a very fast, accurate control loop.

The overall length of the resulting bundled column/sensor wire combination was tested at a length of approximately 2 meters. There are two factors that limit the maximum length of material that can be installed in a column module. The first is the number of coils that can be physical wrapped compactly (see Aluminum Mounting Ring below) in the space reserved for the column module in the instrument design. The second is the maximum heating rate that is desired for a given length of column material. This is due to the relatively high resistance of the metal column material and Ohm's law. The basic trade-off reduces to longer columns having to be heated at lower maximum rates than shorter columns, simply because the amount of power that can be dissipated in the metal tube falls off linearly with increasing length. The 180 μm I.D. column material tested on the prototype has a resistance of ~10 ohms/meter. At an input voltage of 48V the available power for rapid temperature programming drops off rather fast above 2m. However, as column length increases slower heating rates become necessary to extract the maximum resolution from the column, so the trade-off is somewhat balanced.

The components of FIGS. 9 and 9A are as follows:
Lid 903
Electric/Pneumatic End Connector 905
Column Module Electronics 907
Blower Fan 909
Aluminum Support Ring 911
Fiberglass Support Structure 913
Power Resistor 915
Metal Enclosure 917
Supplemental End Heater Coil 919
Fiberglass mounting Strip 921
Valco EU ¹⁄₃₂" Fitting 923
Heated Zone 925

Aluminum Mounting Ring 1001—Shown in FIG. 10 is the relatively low mass aluminum ring around which the bundled column material/sensor wire assembly is tightly and compactly wrapped. Electrical shorts between adjacent coils and the aluminum ring are avoided due to the high-temperature fiberglass sheath that covers the column material and sensor wire.

The ring tested on the prototype was approximately 3" in diameter with a wall thickness of 0.025". The raised lips near the top and bottom edges were implemented to keep the column assembly coils from slipping off the ring.

The high thermal conductivity of aluminum serves a very important function for the overall efficient heating of the column material by dissipating thermal "hot-spots" generated during heating thereby creating a more uniform temperature distribution along the length of the column material. The more uniform the temperature distribution is the more efficient are the resulting component separations.

A second advantage to having the coils compactly wrapped on the aluminum ring is the minimizing of convective surface area and the conservation of heat that naturally occurs due to the intimate contact between adjacent coils. This lowers the overall power requirements for temperature programming as higher temperatures are approached and convective heat losses become the primary mechanism driving the need for increased energy inputs to keep the heating rates constant.

Electric/Pneumatic End Connector—The connector fitting shown in FIGS. 11, 11A and 11B was created to connect the free ends of the coiled column assembly both pneumatically and electrically and at the same time allow the fitting to project into the heated zone while still being attached to the column module.

The Z shaped part 1101 of the connector is made from ¹⁄₁₆" stainless steel sheet metal. Stainless steel is used because of its low thermal conductivity in order to limit the thermal transfer from the heated zone to the column module. An EU.x¹⁄₃₂" fitting 1103 from Valco is pressed into the drilled hole in the face of the fitting opposite the metal enclosure. The free ends of the column connect to the EU fittings using aluminum ferrules 1105 manufactured by Restek. The aluminum material creates a very leak tight connection that doesn't expand or contract like polymeric ferrules and also provides the electrical bridge between the metal column and the end connector fitting. Wires attached to the end connector fitting-screws become the lead wires that get routed to the circuit board for power input.

The connectors are electrically isolated from one another as well as from the metal enclosure by attaching them to a strip of insulating fiberglass sheet that is affixed to the front inside wall of the enclosure. Cut-outs in the wall of the enclosure allow the connectors to protrude without touching the metal edges. Cut-outs in the fiberglass sheet allow the column ends to pass from the inside of the enclosure to the outside.

The nut 1107 that seals the free ends of the column material to the EU.x fitting with the aluminum ferrule is a specially created nut that contains a hose barb type nipple. This nipple provides both a physical and an electrical attachment point for the End-Heater Coils described below.

End-Heater Coil—With the sheathed column material tightly and compactly coiled on the aluminum support ring, a large reduction of surface area is created along the entire length of the column. This reduces convective heat losses and consequently the power required to heat the column at a given linear temperature ramp. However, the free ends of the sheathed column material that are not wrapped on the aluminum support ring have a much larger surface area per unit length of column material exposed to free convection that results in a lower temperature profile relative to the coiled main body of the column material. This differential temperature profile between the free ends and the main body is only exacerbated as the column main body temperature increases. The end result of this is poor chromatography at column temperatures above ~200 deg. C.

To alleviate this problem without implementing a separate actively controlled heater circuit to provide extra heat to the free ends, a heater circuit was created that connects in parallel with the main heater circuit. The heaters consist of pre-wound NiChrom wire coils purchased from Omega Engineering in bulk and then cut to the needed length. One end of the coil is attached to the end connector barbed nut while the other end connects to the fiberglass support structure. The free ends of the column pass through the center of the heater coils thereby providing them with consistent, even heat along their entire length.

The heater coil ends that attach to the fiberglass support structure are connected together with a wire to complete the circuit that may or may not contain a power resistor in series. This power resistor, if needed, controls the current flowing through both coils which limits the heat dissipation in the column free ends.

The bulk coiled NiChrom wire purchased from Omega and tested on the prototype has a resistance of approximately 20 ohms/in. of coil. Since the temperature of the coiled main column body is actively controlled and the end heater coils are operated passively in parallel, the power dissipated in the end heater coils is proportional to the power dissipated in the main column body based on the total resistance of the end heater circuit, which includes a series combination of both heater coils and the optional power resistor. The optimal total series resistance of the end heater circuit was experimentally determined based on a balance of having enough heat being dissipated in the column free ends at a minimum linear heating ramp rate while not overheating the column free ends at a maximum linear heating ramp rate. Chromatographic runs were performed at minimum and maximum linear heating ramp rates with various values of extra resistance in the power resistor and then analyzed to determine the optimal total resistance value for the end heater circuit.

Fiberglass Support Structure—The Fiberglass Support Structure is fabricated from the same material as the Fiberglass Mounting Strip that supports the Electric/Pneumatic End Connectors. The structure is formed from two individual machined fiberglass strips that have slots cut directly in the middle between long ends and half-way through their widths. This allows them to be interleaved at their center slots to form a cross. Slots are also cut in four places, one radius length of the Aluminum Support Ring away from the center slots. This provides a series of circular slots for the Aluminum Support Ring to sit in for mounting in the module.

Blower Fan—A squirrel-cage type blower tan mounts directly beneath the metal enclosure and is used to draw air into the enclosure through small slots machined around the perimeter of the enclosure walls. The fan operates during the idle and cool down phases of an analytical cycle and is turned off during temperature programming.

Column Module Electronics—The electronics that control the temperature modulation of the column material as well as the cooling fan mounts directly beneath the metal enclosure and blower fan on stand-offs. This allows for easy routing of wires to the circuit board while maintaining a compact overall module design.

Detector Module

Figure 12:
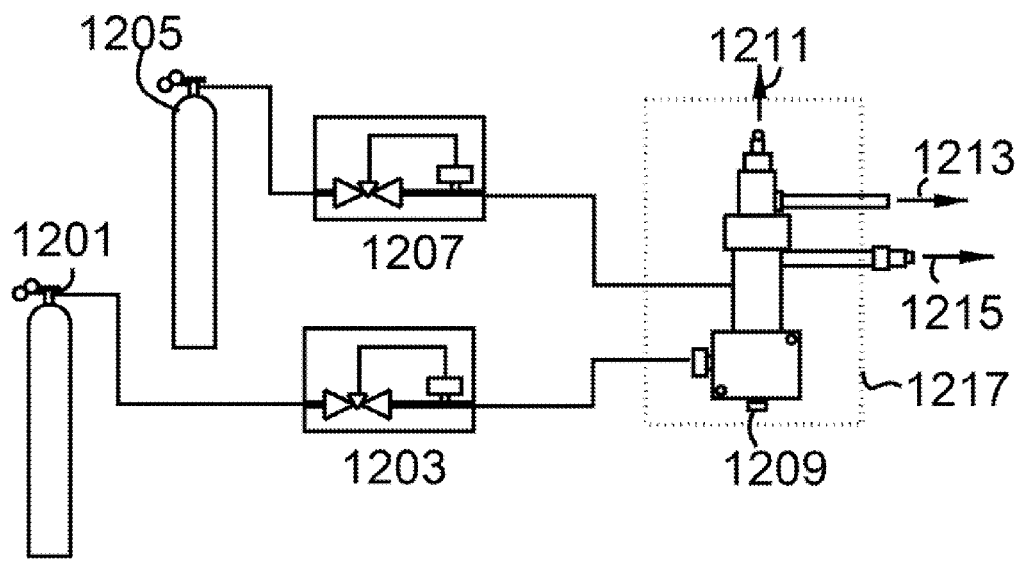
FIG. 12 shows the detector module containing a flame ionization detector

The physical functional diagram for a Detector Module containing a Flame Ionization Detector (FID) is shown in FIG. 12.

Each instrument contains at least one Detector Module per Column Module with a maximum of two Detector Modules per instrument. Some instrument configurations, in theory, could contain two Detector Modules with different types of detectors (e.g. FID and FPD or FID and TCD) for a single Column Module where the effluent from the column is split between the two for simultaneous analysis.

The Detector Module as designed for use in this instrument is a complete, stand-alone device. It contains all electronics and hardware necessary to convert a chemical signal from the effluent of a capillary separation column into a time-based digitized electrical signal where signal magnitude is proportional to chemical concentration. The Detector Module components are as follows:

Hydrogen Source 1201
Electronic Pressure Control 1-1203
Zero Air Source 1205
Electronic Pressure Control 2-1207
Fused Silica From Column 1209
Wired to Igniter Circuit 1211
To Vent 1213
Connect to Electrometer 1215
Heated Zone 1217

The major components that comprise a Detector Module are as follows: detector, heated zone box, pressure control devices for supplying gases to the detector, control electronics, and possibly signal conversion electronics (i.e, electrometer). The detector type designed and tested in the prototype was a FID and is shown in FIGS. 13, 13A, and 13B.

FID Component Description

A description for each critical component that makes up the designed FID is listed below. Please refer to FIG. 13 for clarity.

Base Manifold 1301—The Base Manifold serves as a mounting point for different structural components of the FID and as a secure foundation for attachment to a heater plate inside the heated zone. It also serves as a ported manifold through which the required hydrogen flame fuel and effluent from the capillary separation column can pass to be eventually combusted at the tip of the FID flame tip 1303.

Three internal Valco fitting details are present in the Base Manifold. Two $\frac{1}{32}$" fitting 1305 details are machined on opposite sides of the manifold along the same axis with a connecting through hole. The FID flame tip connects to the top $\frac{1}{32}$" fitting and consists of a short piece of $\frac{1}{32}$" O.D.× 0.016" I.D. stainless steel tubing sealed in the Base Manifold with a stainless steel ferrule. A section of 0.014" O.D. fused silica tubing 1307 from the separation column passes through the bottom $\frac{1}{32}$" fitting detail and terminates inside the FID flame tip at the edge of the tube tip opening. The fused silica tube is sealed to the Base Manifold with a FS.4 fused-silica adapter from Valco.

Entering perpendicular to the axis of the two $\frac{1}{32}$" fitting details is a $\frac{1}{16}$" fitting 1311 detail which connects to the internal through hole. Attached to this fitting detail is the electronic pressure controlled hydrogen flame fuel supply which flows into the annular space between the through hole and the fused silica tube. The gas is forced up into the FID flame tip and is combusted at the point where both the flame tip and fused silica terminate.

Main Body Fitting—Connecting to the Base Manifold is the Main Body Fitting of the FID. This fitting serves many purposes and is a convergence point for many activities that take place within the detector. The Main Body Fitting seals pneumatically to the Base Manifold with a Sealing O-ring 1309 made from either Viton, graphitized Vespel, or pure graphite depending on the temperature at which the module will be operated.

A hole drilled approximately half-way down the length of the fitting perpendicular to the main body cavity provides a 1/16" diameter port where a 1/16" stainless tube is silver soldered. This tube is attached to the outlet of the zero-air electronic pressure control unit 1317 which provides a steady flow of clean air (oxygen) to the Jet Tube tip in order for combustion to take place with the hydrogen exiting the tip.

Protruding from the side of the Main Body Fitting (perpendicular to the plane of the Base Manifold) near the threaded end 1329 is the Side-arm Tube 1333 that creates a conduit for the spring loaded conductor. This conductor carries the electrical signal from the Collector Tube 1327 to the co-axial connector located at the top of the Side-arm Tube. A co-axial cable 1313 attaches to this connector on one end and the electrometer on the other.

Collector Tube—Ceramic Washers 1335—The Collector consists of a flanged tube that resides inside the Main Body Fitting 1331 and "floats" electrically between two insulating ceramic washers. Only the spring loaded conductor 1315 makes electrical contact with the Collector Tube, and because the tube is hollow, a path for combusted exhaust gas is provided through the center of the Collector.

Flanged Igniter Housing—The Flanged Igniter Housing 1325 together with the Coupling Nut 1323 supply the force which sandwiches the Ceramic Washers and Collector Tube against the inner shelf of the Main Body Fitting thereby holding it securely in place. Once the Coupling Nut is securely fastened, the Exhaust Tube 1319 is attached which provides a path for combusted exhaust gas to safely exit the FID and the Instrument enclosure. A 1.5V glow plug 1321 is threaded into the end of the Flanged Igniter Housing and when attached to the igniter circuit creates a red-hot source for lighting the hydrogen flame at the end of the Jet Tube tip.

What is claimed is:

1. A chromatography apparatus comprising;
at least one capillary column,
said capillary column comprising a capillary tubing and a wire coated with an electrically insulating material and a sheath, said capillary tubing and wire being encased within said sheath,
said wire being at least one electrically conductive element co-linear with said capillary tubing,
means for directly resistively heating said capillary tubing, and
means for controlling temperature of said capillary column.

2. The chromatography apparatus of claim 1, further comprising said wire having a diameter of less than about 0.01 inch.

3. The chromatography apparatus of claim 1, further comprising said wire having a diameter of less than about 0.005 inch.

4. The chromatography apparatus of claim 1, further comprising said wire having a diameter of about 0.002 inch.

5. The chromatography apparatus of claim 1, wherein said sheath is fiberglass.

6. The chromatography apparatus of claim 1, wherein said capillary tubing is an electrically resistive material and said means for directly resistively heating further comprising a power supply electrically coupled to said capillary tubing and operable for temperature modulated resistive heating of the capillary column.

7. The chromatography apparatus of claim 1, further comprising said capillary tubing having a size in the range from about 100 μm I.D. to 180 μm I.D.

8. The chromatography apparatus of claim 1, wherein said electrically insulating material is a high temperature polymer.

9. The chromatography apparatus of claim 8, wherein said polymer is a polyimide.

10. The chromatography apparatus of claim 1, further comprising a ring member, said capillary column being coiled on said ring member.

11. The chromatography apparatus of claim 10, wherein said wire is a sensor wire and is electrically connected to a temperature modulation circuit.

12. The chromatography apparatus of claim 11, wherein said ring member is a support member of a relatively low mass aluminum and wherein said capillary tubing and said sensor wire are bundled tightly and compactly wrapped around said ring member.

13. The chromatography apparatus of claim 12, further comprising said ring having raised lips proximate its top and bottom edges and wherein said capillary column is retained on said ring within said raised lips.

14. The chromatography apparatus of claim 12, further comprising said ring having a wall thickness of under 0.1 inch.

15. The chromatography apparatus of claim 12, further comprising said ring having a wall thickness of under about 0.05 inch.

16. The chromatography apparatus of claim 12, further comprising said ring having a wall thickness of under about 0.025 inch.

17. The chromatography apparatus of claim 12, wherein said sensor wire is then fitted with low resistance lead wires and said sensor wire is in intimate, electrically insulated contact with said capillary tubing, whereby the intimate contact between the sensor wire and said capillary tubing and the low mass of each, provides a very small thermal transport delay between said sensor wire and said capillary tubing, and provides a very fast, accurate temperature feedback control loop.

18. The chromatography apparatus of claim 12, further comprising an electric-pneumatic end connector affixed to each end of said capillary tubing and providing an electrical contact with said sensor wire and a fluid inlet to a first end said capillary tubing and a fluid outlet to a second end of said capillary tubing, each of said end connectors projecting into a heated zone while still being attached to said capillary tubing.

19. The chromatography apparatus of claim 18, wherein said end connectors are stainless steel sheet metal and said end connectors are supported by an aluminum material support member, said support member providing an electrical bridge between the capillary tubing and said end connectors, and further comprising electrically conductive wires attached to said end connectors and routed to a circuit board for power input.

20. The chromatography apparatus of claim 18, further comprising a detector module, said detector module being within said heated zone and further comprising a member selected from the group comprising a flame ionization detector, a flame photometric detector, a thermal conductivity detector, and combinations thereof.

21. The chromatography apparatus of claim 20, wherein the overall length of the capillary tubing and sensor wire combination is on the order of two meters, or greater, said ring, capillary tubing and sensor wire forming a column module, and further comprising cooling means relative to the column module, wherein said cooling means is a blower fan positioned to cool at least one component within said heated zone relative to the column module, a micro-flame detector, a heater, said heater being in heat transfer relationship with said micro-flame detector relative to the connection between a sample processing module and the detector module and providing heat to said heated zone, means for operating the cooling means during the idle and cool down phases of an analytical cycle and turned turning off the cooling means during temperature programming, and heating control means to control the maximum heating rate that is desired for a given length of said capillary tubing, wherein said maximum heating rate is a predetermined value based on the high resistance of the metal capillary column material and Ohm's law, and wherein power dissipation is inversely related to length of said capillary tubing.

* * * * *